(12) United States Patent
Persen et al.

(10) Patent No.: US 7,324,850 B2
(45) Date of Patent: Jan. 29, 2008

(54) METHOD AND APPARATUS FOR COMMUNICATION BETWEEN A HANDHELD PROGRAMMER AND AN IMPLANTABLE MEDICAL DEVICE

(75) Inventors: Kenneth H. Persen, Maple Grove, MN (US); Jeffrey A. Von Arx, Minneapolis, MN (US); Dennis Eric Larson, White Bear Lake, MN (US); Vineel Vallapureddy, Saint Paul, MN (US); Matthias Daniel Woellenstein, Minneapolis, MN (US); Jason Dean Hein, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 401 days.

(21) Appl. No.: 10/835,043

(22) Filed: Apr. 29, 2004

(65) Prior Publication Data

US 2005/0245992 A1    Nov. 3, 2005

(51) Int. Cl.
*A61N 1/36* (2006.01)
(52) U.S. Cl. .............. 607/30; 607/59; 607/32; 607/60
(58) Field of Classification Search ........... 607/30–32, 607/59–60; 128/903
See application file for complete search history.

(56) References Cited

U.S. PATENT DOCUMENTS

| 5,311,449 | A | 5/1994 | Adams |
| 6,006,132 | A | 12/1999 | Tacker, Jr. et al. |
| 6,249,703 | B1 | 6/2001 | Stanton et al. |
| 6,381,496 | B1 | 4/2002 | Meadows et al. |
| 6,524,240 | B1 * | 2/2003 | Thede .................. 600/300 |
| 6,574,503 | B2 * | 6/2003 | Ferek-Petric ............ 600/523 |
| 6,622,048 | B1 * | 9/2003 | Mann et al. ............. 607/46 |
| 7,203,549 | B2 * | 4/2007 | Schommer et al. ........ 607/60 |
| 2001/0041920 | A1 | 11/2001 | Starkweather et al. |
| 2001/0051787 | A1 * | 12/2001 | Haller et al. ............. 604/66 |
| 2002/0002326 | A1 | 1/2002 | Causey, III et al. |
| 2002/0072785 | A1 | 6/2002 | Nelson et al. |
| 2002/0082665 | A1 | 6/2002 | Haller et al. |
| 2002/0173830 | A1 | 11/2002 | Starkweather et al. |
| 2003/0055406 | A1 | 3/2003 | Lebel et al. |
| 2003/0093127 | A1 * | 5/2003 | Dalal ..................... 607/32 |
| 2003/0144711 | A1 | 7/2003 | Pless et al. |
| 2003/0171791 | A1 | 9/2003 | KenKnight et al. |
| 2004/0204633 | A1 * | 10/2004 | Rentea et al. ............ 600/300 |
| 2005/0075688 | A1 * | 4/2005 | Toy et al. ................ 607/60 |
| 2007/0156033 | A1 * | 7/2007 | Causey et al. ........... 600/300 |

* cited by examiner

Primary Examiner—Carl Layno
(74) Attorney, Agent, or Firm—Schwegman, Lundberg & Woessner, P.A.

(57) ABSTRACT

Systems and methods for telemetric communication between a handheld programmer and an implantable medical device are disclosed. A preferred embodiment comprises a user-friendly, color, touch-sensitive screen that allows the user to visually observe and control the handheld's operation. The handheld further comprises an internal and/or external analytical means to provide robust analytical capabilities. Some embodiments of a system disclosed herein can be configured as a component of an Advanced Patient Management System that helps better monitor, predict and manage chronic diseases.

48 Claims, 3 Drawing Sheets

METHOD AND APPARATUS FOR COMMUNICATION BETWEEN A HANDHELD PROGRAMMER AND AN IMPLANTABLE MEDICAL DEVICE

TECHNICAL FIELD

The present device relates generally to implantable medical devices and particularly, but not by way of limitation, to an external device that can communicate with an implantable device to monitor and control its operation.

BACKGROUND

When functioning properly, the human heart maintains its own intrinsic rhythm based on physiologically-generated electrical impulses. It is capable of pumping adequate blood throughout the body's circulatory system. Each complete cycle of drawing blood into the heart and expelling it is referred to as a cardiac cycle.

However, some people have abnormal cardiac rhythms, referred to as cardiac arrhythmias. Such arrhythmias result in diminished blood circulation. Arrhythmias can occur in the upper chambers of the heart—the atria, or the lower chambers of the heart—the ventricles. However, ventricular arrhythmias present the most serious health risk as they can lead to rapid death from the lack of circulation. Arrhythmias can be subdivided further into specific conditions of the heart that represent vastly different manifestations of abnormal cardiac rhythm. These conditions are bradycardia, or a slow heartbeat, and tachycardia, or a fast heart beat.

One mode of treating a cardiac arrhythmia uses an implantable medical device ("IMD"). Such implantable medical devices include pacemakers, also referred to as pacers, and defibrillators. The traditional use of a pacemaker is to treat a person with bradycardia. In other words, pacemakers help speed up the cardiac cycle of a person whose heart beats too slowly. Pacers accomplish this by delivering timed sequences of low energy electrical stimuli, called pace pulses, to the heart. Such stimuli are delivered via an intravascular lead wire or catheter (referred to as a "lead") having one or more electrodes disposed in or about the heart.

In comparison to a pacemaker, an implanted defibrillator applies a much stronger electrical stimulus to the heart. This is sometimes referred to as a defibrillation countershock, also referred to simply as a "shock." The shock changes ventricular fibrillation to an organized ventricular rhythm or changes a very rapid and ineffective cardiac rhythm to a slower, more effective rhythm. Defibrillators help treat cardiac disorders that include ventricular fibrillation, ventricular tachycardia, atrial fibrillation, and atrial flutter. These inefficient or too rapid heartbeats reduce the pumping efficiency of the heart and thereby diminish blood circulation. The countershock delivered by the defibrillator interrupts the tachyarrhythmia, allowing the heart to re-establish a normal rhythm for the efficient pumping of blood.

The cardiac rhythm management devices discussed above may also include a wireless sending and receiving capability that permits an external programmer or controller to send instructions and receive data from the implanted device. Such a controller permits communication with the implanted device without the need to physically access the implanted device. Such controllers are known for use by physicians or other medical personnel to monitor and control the function of the implanted device.

The monitoring or interrogation mode of an external programmer or controller is used primarily as a follow-up tool to evaluate the implanted device and patient during subsequent office visits. This mode is very important for patients who have an implanted defibrillator because, typically, no other means exist to efficiently evaluate the condition or effectiveness of the device. Normally, patients have to schedule periodic and frequent visits with a clinician to have the device checked and may require surgery if an anomaly is detected.

Such controllers, with limited sets of commands, are known to permit a patient to have some control over the function of the implanted device. However, patient-operated controllers may require an electrical cord providing power from a wall outlet or other external power source and may include text based messages to communicate with the patient regarding the status of the implanted device and to acknowledge receipt of an instruction by the implanted device.

U.S. Pat. No. 5,311,449 to Adams discloses a sterilizable, hand-held programmer/interrogator for communication with an implanted defibrillator. The device uses radio frequency (RF) telemetry to communicate and transmit data to the defibrillator. Device programming and interrogation are controlled by "function control keys," an "electromechanical key" that controls the device's functionality and a "display." The display allows retrieved data to be shown serially on two lines of sixteen characters each. The '449 patent does not disclose a touch-sensitive, color screen as a display option or the ability to communicate with other sensors adapted to monitor other physiological parameters.

U.S. Pat. No. 6,006,132 to Tacker, Jr., et al., discloses a non-implantable communication device that is hand-held and adapted to communicate with an implantable atrial defibrillation device to monitor the status of the device and program its operation. According to the '132 patent, the hand-held communication device is adapted to provide positive feedback to the patient when making an external command by including both an acknowledgement that the command was received and a description of the task being performed by the implantable device in response to the command. However, the '132 patent does not disclose a use of the hand-held communication device beyond its compatibility with an atrial defibrillator. In addition, the disclosed device is essentially a portable communication device with control commands that are "vastly limited as compared to the control commands which may be derived from the external programmer," preferably, "simple mode select commands, a therapy sequence control command, and a status request control command." See '132 patent, Col. 5, ll. 16-21. Consequently, the '132 patent does not disclose or teach a hand-held external programmer with robust command and interrogation capabilities.

U.S. Pat. No. 6,249,703 to Stanton et al. also discloses a portable programmer. The programmer provides tactile, audible, and visible feedback to the user to convey information regarding the proper (or improper) operation of the programmer and the implanted device. However, as shown in FIG. 2 of the patent, user input keys 19, 20, 21, and 22 are limited to pre-programmed uplink and downlink operations and are generally incapable of providing robust input or device interrogation means.

U.S. Pat. No. 6,381,496 to Meadows et al. describes a hand-held programmer for implantable or non-implantable devices that includes an electronically stored set of transmittable operational parameters for the device. Suitable devices include spinal cord stimulators, neural stimulators and sensors, deep brain stimulators, cochlear stimulators, drug delivery systems and muscle tissue stimulators. The programmer is further adapted to receive telemetric data from the device and, based on that input, change the device's operational parameters within certain pre-defined limits. Telemetry may be accomplished with modulated RF signals. The patent further discusses a touch screen display as one way to control the operation of the programmer. However, the '496 patent does not discuss the programmer as a device with robust analytical capabilities accessible by the clinician or patient. Nor does the patent discuss the programmer as a component of a larger network of medical devices. In essence, the '496 patent addresses the need of providing a device with context switching, which is changing one set of operational parameters to another set.

U.S. published patent application no. 2001/0041920, application Ser. No. 09/769,201, describes a hand-held communication device capable of transmitting data to or receiving data from a medical device, preferably an infusion pump. The transmitted data is primarily directed towards replacement or upgrade software for the medical device. In addition, the communication device is capable of transmitting patient definable parameters that can be used to modify the treatment or monitoring performed by the medical device. However, the application does not teach or disclose the use of the communication device as a component of a network of devices or a robust analytical tool capable of displaying device parameters and functions for access and modification by the patient or a clinician.

Similarly, U.S. published patent application no. 2001/0173830, application Ser. No. 09/768,207, describes a communication device of the type described in the '201 application discussed above. However, this application focuses on improving the communication link between the IMD and the communication device by minimizing the risk of synchronization loss between transmitted and received bits of data.

U.S. published patent application no. 2002/0082665, application Ser. No. 09/765,484, describes a system for monitoring and programming an implantable medical device. However, the system comprises a communication module operably connected to a mobile telephone and/or a personal digital assistant ("PDA"). The application does not teach or disclose a communication unit that can program an PDA without the need for a wireless phone or PDA to bridge communication between the MD and a remote computer system or health care provider.

Another example of a hand-held device for use with an implantable medical device is discussed in U.S. published patent application no. 2002/0072785, application Ser. No. 10/068,478. However the '478 application discusses the use of a hand-held personal data manager ("PDM") that essentially serves as a data messenger between the implantable medical device, a programmer and a networked data center. The '478 application does not teach or disclose a hand-held programmer that supplants the need for a PDM data bridge.

None of these references discloses or teaches the functionality of a programmer in the size of a handheld device. In fact, the programmers in the prior art act primarily as repeaters, but are not adapted to process telemetry data and present such data in a user-friendly format. As known to those of skill in the art, a repeater comprises a system and device that electronically collects information from an implantable medical device and transmits that information to a centralized computer network or server for analysis.

In addition, existing programmers are bulky and not very portable. An advantage of the programmer described herein is that it is portable, lightweight and small. Therefore, in addition to improved portability, the programmer of the present invention will significantly reduce the cost of production for manufacturing an IMD programmer.

Thus, for these and other reasons, there is a need for a compact programmer for an implantable medical device that is easily accessible by touch-screen control, employs RF telemetry to provide robust communication and data analysis between the programmer and device, and is adaptable as a component of a patient management network.

SUMMARY

According to one aspect of the invention, there is provided a method and device for robust, telemetric communication between a user-friendly, handheld programmer and an implantable medical device. The handheld is adapted to accept changes to the information presented and reprogram the implantable medical device with the new information. As used herein, a "clinician" can be a physician, physician assistant (PA), nurse, medical technologist, or any other patient health care provider.

A handheld programmer like a PDA or tablet pc will communicate with an implantable medical device through telemetry. The system is adapted to support short-range inductive telemetry and long range RF telemetry through hardware in the handheld. The handheld may be further adapted to perform a body surface electrocardiogram ("ECG"). The system programmer may comprise custom hardware or hardware known in the art that is capable of providing the device with suitable telemetric means.

To improve user access, the programmer includes a touch-sensitive screen and a color display to accept input or display information. The programmer may also include a compatible cradle. In addition, the programmer can store information and is analytically robust enough to display information in real time traces from the device and also communicate current parameter settings.

Users will also be able to perform diagnostic tests using the handheld. This device can be used during follow-up sessions to monitor or reprogram the implantable device. Re-programming may also occur remotely. In such an embodiment, the IMD may be monitored and re-programmed by a clinician or patient management system at a remote location via the telemetric capabilities of the handheld.

In another embodiment, the handheld communicates with the implantable medical device using induction technology. To be effective, such technology is typically limited to short-range inter-device communication.

In yet another embodiment, the handheld communicates with the implantable medical device using RF technology. The use of RF technology allows longer-range communication between the handheld and the medical device.

Preferably, the handheld comprises a color, touch-sensitive screen that allows the user to visually observe and control the handheld's operation. The screen in this embodiment may include a liquid crystal display or any other type of color display known in the art to provide touch-screen functionality.

In a further embodiment, the handheld may be adapted to serve as a data and/or analytical bridge between an implantable medical device and a more traditional programmer for such a device.

In yet a further embodiment, the handheld may be adapted or adaptable as a component of a network of other handhelds or implantable devices. Configured in this manner, the handheld is adapted to consult and analyze data beyond the functional limits of the handheld itself. Such a network may include an Advanced Patient Management system.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention, which is set forth in the following claims.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present disclosure.

DETAILED DESCRIPTION

In the following detailed description, reference is made to the accompanying drawings that form a part hereof, and in which are shown by way of illustration specific embodiments or examples. These embodiments may be combined, other embodiments may be utilized, and structural, logical, and electrical changes may be made without departing from the spirit and scope of the present invention. The following detailed description is, therefore, not to be taken in a limiting sense, and the scope of the present invention is defined by the appended claims and their equivalents.

The present method and device are described with respect to a handheld programmer for an implantable medical device that is adapted to wirelessly communicate with the medical device. The programmer may further be adapted to communicate with a network of implantable devices. Such a network may be mediated by or integrated with an Advanced Patient Management ("APM") system. The term "patient management" refers to the process of creating and collecting patient specific information, storing and collating the information, and generating actionable recommendations to enable the predictive management of patients with chronic disease.

Figure 1:
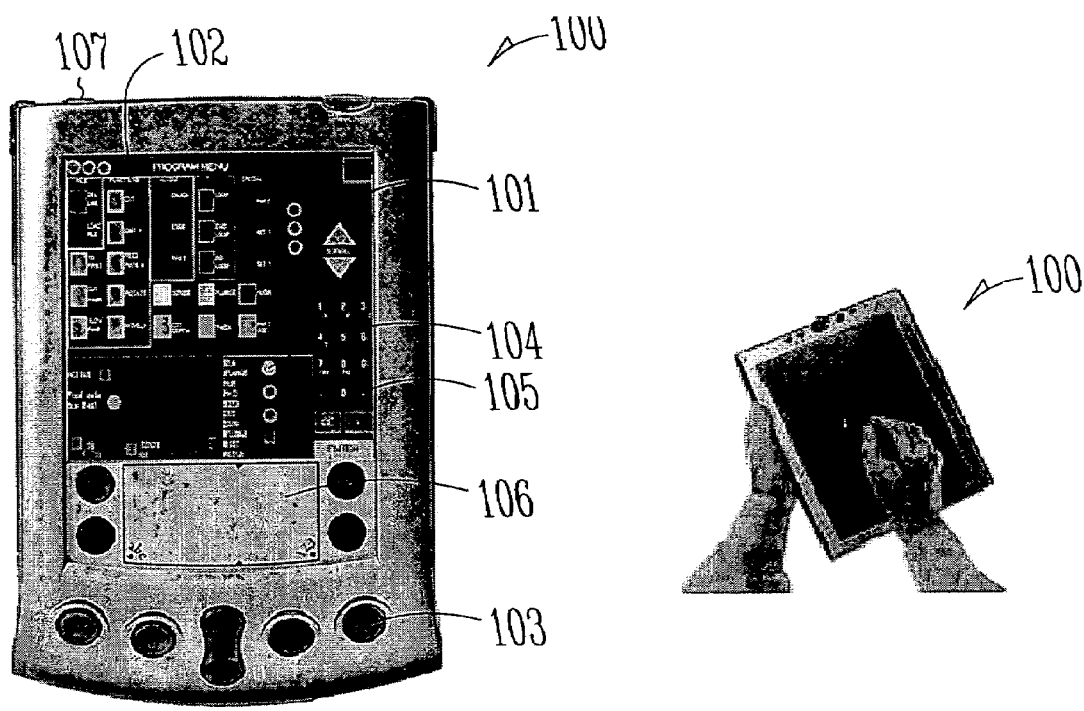
FIG. 1 is a diagram illustrating generally, among other things, a handheld programmer configured as a PDA or tablet pc comprising a color, touch-sensitive screen to program and monitor the function of an implantable medical device.

FIG. 1 is a diagram illustrating generally, among other things, a handheld programmer configured as a PDA or tablet pc 100. The PDA disclosed herein is a modification of a Palm™ style PDA. In this embodiment, the programmer 100 comprises a color, touch-sensitive screen 101 that allows the clinician or patient to program and monitor a function 102 of an implantable medical device. The programmer 100 may further comprise means to change the programming menu or monitoring options by selecting pre-set programming functions or parameters that can be activated by engaging, for example, button 103. As further shown in FIG. 1, the programmer may be adapted to provide the patient or clinician with the ability to interrogate the implantable medical device to determine the status of its operation or to provide patient diagnostic information. For example, the implantable medical device may be adapted to sense a physiological parameter, like thoracic impedance, as a predictor of a pending asthma attack. By using the touch-sensitive screen 101, the patient or clinician may be able to monitor this parameter in real-time and take pre-emptive measures before such an attack becomes acute. Monitoring may take the form of an alpha 104, numeric 105 or graphical feedback display (not shown). The programmer 100 may further be adapted to allow the patient or clinician the ability to customize data input or display by alphanumeric input means. For example, the programmer may be programmed through an alphanumeric pad 106 to interrogate the implantable medical device at specific times of the day by entering those times via the alphanumeric input pad 106. The programmer 100 may be further programmed to transmit interrogated data to a computer network accessible by a clinician. Transmission of interrogated or other data may be accomplished telemetrically 107. Inductive and/or RF telemetry are contemplated as suitable transmission means. However, those skilled in the art will appreciate that other means exist, like infrared means for example, to transmit data that are consistent with the goals and objectives of the present disclosure. The reader should understand the embodiments of FIG. 1 are for illustrative purposes only and are not intended to define or limit the scope of the present disclosure.

Figure 2:
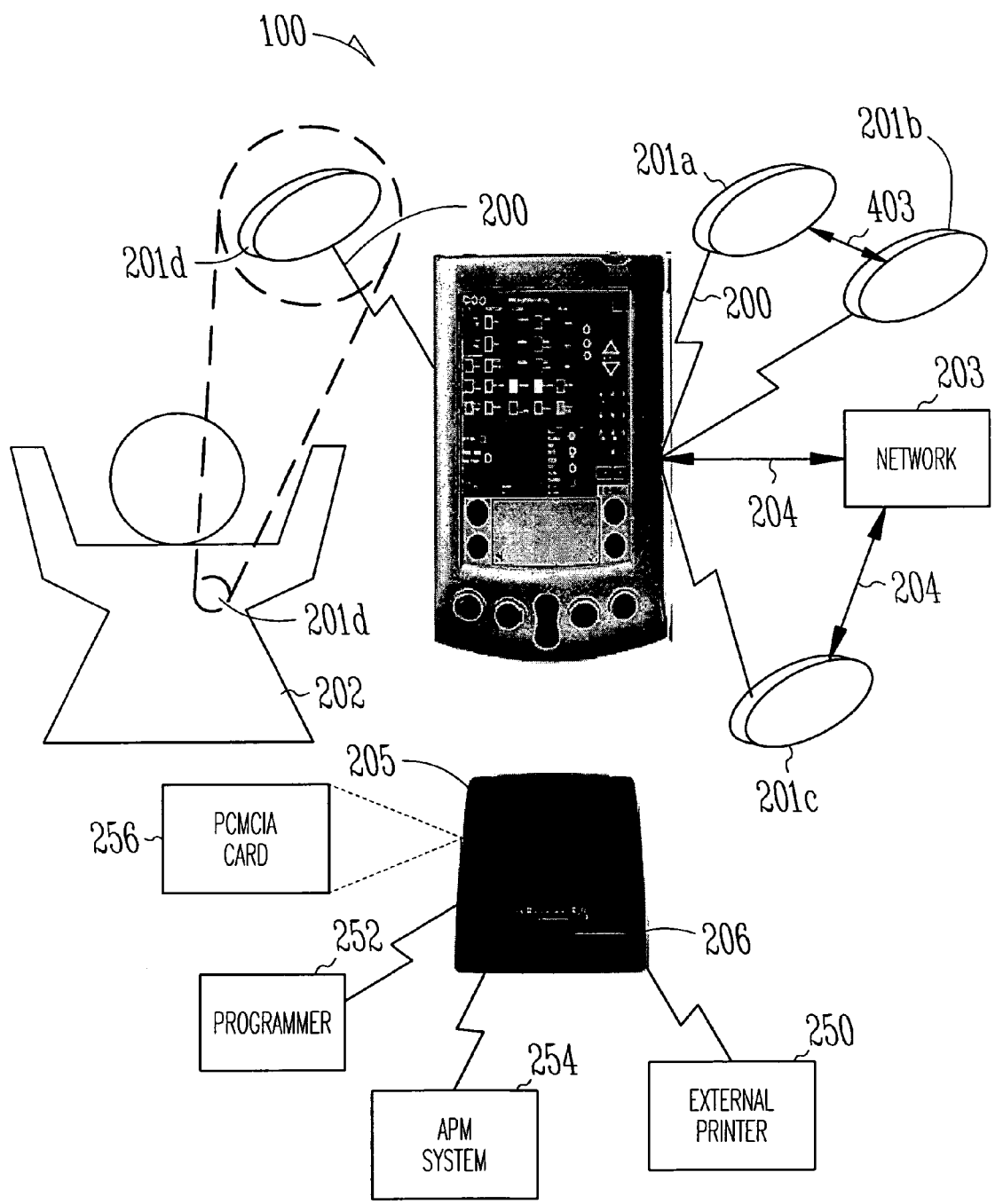
FIG. 2 is a schematic/block diagram illustrating generally, among other things, an embodiment of the handheld programmer with a compatible cradle in electronic communication with an implantable medical device and/or a network of such devices as components of a computer network.

FIG. 2 is a schematic/block diagram illustrating generally another embodiment of the handheld programmer 100 adaptable to communicate 200 with other implantable medical devices 201a, 201b and 201c. Such devices may be implanted 201d in a patient 202 to monitor multiple physiological parameters. For example, Muscle Sympathetic Nerve Activity (MSNA) may be measured with an injectable, microelectrode-sensing device. Consequently, the programmer 100 may be adapted to monitor and communicate 200 with a suite of medical devices 201a, 201b, 201c and 201d that are implanted in a patient 202 and analyze the data reported by each medical device to provide a more comprehensive assessment of patient health. The programmer 100 also may be adapted to analyze and report on multiple medical devices 201a, 201b and 201c implanted in different patients. One method of accomplishing this is by utilizing a computer network 203 to store and analyze the data 204 sent to and received from the programmers of different patients. This will allow the clinician to simultaneously monitor the status of a population of patients to help identify and evaluate environmental stressors and other factors that may affect groups of patients. In addition, the programmer 100 may be programmable to work with more than one patient's implantable medical device so the programmer 100 is interchangeable between patients. Of course, safety controls could be implemented to prevent unauthorized or dangerous use of the programmer 100 by a patient or clinician in this embodiment. One such safety control might include pre-set programming limits for the device that can be changed only by the clinician or by the clinician in combination with the manufacturer of the programmer and/or medical device. The programmer 100 also may be adapted with a compatible cradle 205. In this embodiment, the cradle 205 may serve as a connectivity port or an energy source. The connectivity port might include an Ethernet™ port, an infrared port, or other wireless ports (not shown). The cradle 205 may be adapted with a built-in printer 206, including a strip chart recorder ("SCR") to provide a hard copy of the data stored in or mediated by the programmer 100. The cradle can include a printer adapted to print standard, 8 ½ by 11 inch paper, or to electronically communicate with an external printer 250, another programmer 252, or an APM system 254. The cradle can include a PCMCIA card 256.

Figure 3:
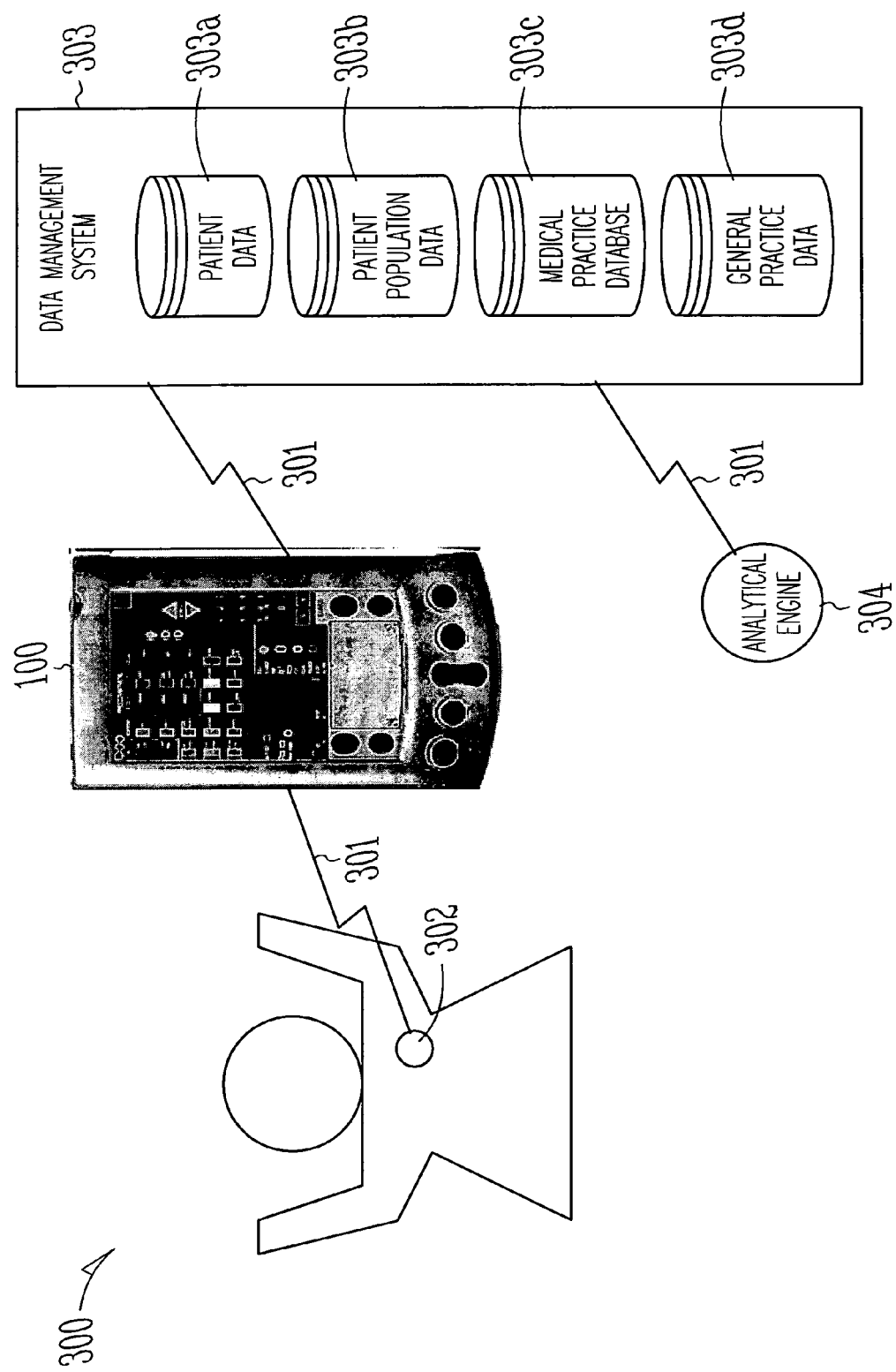
FIG. 3 is a schematic/block diagram illustrating generally, among other things, another embodiment of the handheld programmer in electronic communication with an implantable medical device and an APM system comprising medical and patient databases and an analytical engine.

FIG. 3 is a schematic/block diagram illustrating generally another embodiment of the handheld programmer 100 as a component of a communicative 301 APM system 300. APM is a system that helps patients, their physicians and their families to better monitor, predict and manage chronic diseases. APM is particularly useful in maintaining long-term data continuity and combining information from medical devices, including the method and apparatus for communication between a handheld programmer 100 and an implantable medical device 302 disclosed herein, with patient data from other medical databases. In the embodiment shown in FIG. 3, the APM system 300 comprises three primary components: 1) a handheld programmer 100; 2) an implantable medical device 302, including at least one sensor adapted to monitor physiological functions; 3) a data management system 303 comprising patient 303a, 303b and medical 303c, 303d databases; and 4) an analytical engine 304 that analyzes data from the data management module. APM is designed to support physicians and other clinicians in using a variety of different devices, patient-specific and non-specific data, along with medication therapy, to provide the best possible care to patients.

All the embodiments of the handheld programmer described above may include means to store data. Typically, such means include computer memory systems or devices, like a PCMCIA card. Such cards are also capable of providing communications and data storage capabilities to the programmer.

The programmer may be further adapted to provide a body surface ECG. A body surface ECG is the reflection of the electrical activity of the heart on the surface of the human body.

The various embodiments described above are provided by way of illustration only and should not be construed to limit the invention. The above-described embodiments may be used in combination with each other. Those skilled in the art will readily recognize various modifications and changes that may be made to the present invention without following the example embodiments and applications illustrated and described herein, and without departing from the true spirit and scope of the present invention, which is set forth in the following claims and their equivalents. In the appended claims, the terms "including" and "in which" are used as the plain-English equivalents of the respective terms "comprising" and "wherein."

What is claimed is:

1. An apparatus comprising:
   a handheld programmer for wireless analysis and programming of an implantable device, the programmer having a size adapted to be hand held;
   a transmitter, included as part of the programmer;
   a receiver, included as part of the programmer; and
   a color, touch-sensitive display screen, located on the programmer; and
   wherein the programmer is configured to display data electronically communicated from at least one implantable medical device, and wherein at least some of the data is displayed in real-time, wherein the data comprises data indicative of operation of the at least one implantable medical device, and wherein the data comprises data indicative of parameter settings of the at least one implantable medical device.

2. The apparatus of claim 1, wherein the programmer is accessible by a clinician.

3. The apparatus of claim 1, wherein the programmer is accessible by a patient.

4. The apparatus of claim 3, wherein the programmer includes pre-set programming limits.

5. The apparatus of claim 1, wherein the programmer comprises a PCMCIA card.

6. The apparatus of claim 1, wherein the programmer comprises a personal digital assistant.

7. The apparatus of claim 1, wherein the programmer comprises a tablet pc.

8. The apparatus of claim 1, wherein the programmer is adapted as a data bridge to a traditional programmer for an implantable medical device.

9. The apparatus of claim 1, wherein the programmer is adapted as an analytical bridge to a traditional programmer for an implantable medical device.

10. The apparatus of claim 1, wherein the programmer is adapted as a data and analytical bridge to a traditional programmer for an implantable medical device.

11. The apparatus of claim 1, wherein the device is adapted to electronically store data received from the at least one implantable medical device.

12. The apparatus of claim 1, wherein the programmer is adapted to program the at least one implantable medical device.

13. The apparatus of claim 12, wherein the programmer is adapted to remotely program the at least one implantable medical device.

14. The apparatus of claim 1, wherein the programmer is adapted to interrogate the at least one implantable medical device.

15. The apparatus of claim 1, wherein the programmer is adapted to diagnose operation of the at least one implantable medical device.

16. The apparatus of claim 1, wherein the programmer is adapted to electronically communicate with multiple implantable medical devices.

17. The apparatus of claim 16, wherein the programmer is adapted to electronically communicate with multiple implantable medical devices that are implanted in at least one patient.

18. The apparatus of claim 16, wherein the programmer is adapted to electronically communicate with multiple implantable medical devices that are implanted in more than one patient.

19. The apparatus of claim 1, wherein the programmer is adapted to electronically communicate with a computer network.

20. The apparatus of claim 1, wherein the programmer is adapted to electronically communicate with an Advanced Patient Management system.

21. The apparatus of claim 1, wherein the programmer is adapted to analyze data electronically communicated from at least one implantable medical device.

22. The apparatus of claim 1, wherein the data comprises data indicative of operation of the handheld programmer.

23. The apparatus of claim 1, wherein the transmitter includes inductive telemetry.

24. The apparatus of claim 1, wherein the transmitter includes include RF telemetry.

25. The apparatus of claim 1, wherein the transmitter includes infrared telemetry.

26. The apparatus of claim 1, wherein the receiver includes inductive telemetry.

27. The apparatus of claim 1, wherein the receiver includes RF telemetry.

28. The apparatus of claim 1, wherein the receiver includes infrared telemetry.

29. The apparatus of claim 1, wherein the display screen comprises a liquid crystal display.

30. The apparatus of claim 1, wherein the programmer is further adapted to be a component of a computer network.

31. The apparatus of claim 30, wherein the network comprises multiple haudheld programmers.

32. The apparatus of claim 30, wherein the network comprises multiple handheld and implantable medical devices.

33. The apparatus of claim 30, wherein the programmer comprises a component of a patient management system.

34. The apparatus of claim 1, comprising a compatible cradle and wherein the programmer is adapted for the compatible cradle.

35. The apparatus of claim 34, wherein the cradle is adapted to provide energy to the handheld programmer.

36. The apparatus of claim 34, wherein the cradle includes a printer.

37. The apparatus of claim 36, wherein the cradle includes a printer adapted to print standard, 8½ by 11 inch paper.

38. The apparatus of claim 36, wherein the cradle includes a SCR printer.

39. The apparatus of claim 34, wherein the cradle is adapted to electronically communicate with another programmer.

40. The apparatus of claim 34, wherein the cradle is adapted to electronically communicate with an Advanced Patient Management (APM) system.

41. The apparatus of claim 34, wherein the cradle is adapted to electronically communicate with an external printer.

42. The apparatus of claim 34, wherein the cradle is adapted to electronically communicate.

43. The apparatus of claim 42, wherein the cradle comprises at least one connectivity port.

44. The apparatus of claim 43, wherein the port comprises an Ethernet™ port.

45. The apparatus of claim 43, wherein the port comprises an infrared port.

46. The apparatus of claim 43, wherein the port comprises a wireless port.

47. An apparatus comprising:
a handheld programmer for wireless analysis and programming of an implantable device,
the programmer having a size adapted to be hand held, wherein the programmer is further adapted to be a component of a computer network that comprises multiple implantable medical devices;
a transmitter, included as part of the programmer;
a receiver, included as part of the programmer; and
a color, touch-sensitive display screen, located on the programmer; and
wherein the programmer is adapted to display data electronically communicated from at least one implantable medical device, wherein the data comprises data indicative of operation of the at least one implantable device.

48. An apparatus comprising:
a handheld programmer for wireless analysis and programming of an implantable device, the programmer having a size adapted to be hand held, wherein the programmer is adapted to be a component of a computer network and wherein the programmer comprises a component of a patient management system;
a transmitter, included as part of the programmer;
a receiver, included as part of the programmer; and
a color, touch-sensitive display screen, located on the programmer;
wherein the programmer is adapted to display data electronically communicated from at least one implantable medical device, wherein the data comprises data indicative of operation of the at least one implantable device; and
wherein the patient management system comprises:
an implantable medical device including at least one sensing module adapted to monitor at least one physiological function;
a data management module comprising medical practice data, general practice data, patient data and patient population data and adapted to electronically communicate with an analysis module;
an analysis module adapted to analyze data from and electronically communicate with the data management module; and
the handheld programmer, wherein the haudheld programmer is adapted to electronically communicate with the implantable medical device and the data management module.

* * * * *

UNITED STATES PATENT AND TRADEMARK OFFICE
CERTIFICATE OF CORRECTION

PATENT NO. : 7,324,850 B2
APPLICATION NO. : 10/835043
DATED : January 29, 2008
INVENTOR(S) : Persen et al.

It is certified that error appears in the above-identified patent and that said Letters Patent is hereby corrected as shown below:

In column 8, lines 1–2, in Claim 1, delete ", and wherein at least some of the data is displayed in real-time" and insert the same on Col. 8, Line 6, after "device".

In column 9, line 2, in Claim 24, after "includes" delete "include".

In column 9, line 16, in Claim 31, delete "haudheld" and insert -- handheld --, therefor.

In column 10, line 13, in Claim 47, delete "adapted" and insert -- configured --, therefor.

In column 10, line 17, in Claim 47, after "device" delete "." and insert -- , and wherein at least some of the data is displayed in real-time. --, therefor.

In column 10, line 46, in Claim 48, delete "haudheld" and insert -- handheld --, therefor.

Signed and Sealed this

Eighth Day of July, 2008

JON W. DUDAS
*Director of the United States Patent and Trademark Office*